United States Patent [19]

Jadamus et al.

[11] 4,146,738

[45] Mar. 27, 1979

[54] PROCESS FOR THE TELOMERIZATION OR OLIGOMERIZATION OF ACYCLIC CONJUGATED DIOLEFINS

[75] Inventors: Hans Jadamus; Klaus Diebel, both of Marl, Fed. Rep. of Germany

[73] Assignee: Chemische Werke Huels, Aktiengesellschaft, Marl, Fed. Rep. of Germany

[21] Appl. No.: 819,193

[22] Filed: Jul. 26, 1977

[30] Foreign Application Priority Data

Aug. 5, 1976 [DE] Fed. Rep. of Germany ....... 2635250

[51] Int. Cl.$^2$ ...................... C07L 47/06; C07L 41/10; C07L 11/00
[52] U.S. Cl. ............................... 568/690; 260/677 R; 252/411 R; 252/416; 252/431 P
[58] Field of Search ....... 260/614 AA, 632 R, 612 D, 260/612 R, 677; 568/904

[56] References Cited

U.S. PATENT DOCUMENTS

| | | | |
|---|---|---|---|
| 3,530,187 | 9/1970 | Shryne | 260/614 AA X |
| 3,670,032 | 6/1972 | Romanelli | 260/614 AA |
| 3,691,249 | 9/1972 | De Young | 260/677 R |
| 3,769,352 | 10/1973 | Romanelli | 260/614 AA |
| 3,925,497 | 12/1925 | Josey et al. | 260/677 R |
| 3,992,456 | 11/1976 | Atkins et al. | 260/614 AA |
| 4,021,383 | 5/1977 | Cuscurida et al. | 260/614 AA |

FOREIGN PATENT DOCUMENTS

| | | | |
|---|---|---|---|
| 1248593 | 10/1971 | United Kingdom | 260/614 AA |
| 1354507 | 5/1974 | United Kingdom | 260/614 AA |

OTHER PUBLICATIONS

Takahashi et al. I, Bull. Chem. Soc, Japan, 41, pp. 454–460 (1968).
Takahashi et al. II, Tetrahedron Letters, No. 26, pp. 2451–2453, 1967.

*Primary Examiner*—Howard T. Mars
*Attorney, Agent, or Firm*—Millen & White

[57] ABSTRACT

Acyclic conjugated diolefins of 4–6 carbon atoms can be telomerized or oligomerized by themselves or with H-acidic compounds in the presence of an activated palladium (triarylphosphine) catalyst prepared by oxidatative removal of 1–3.5 molar equivalents of triphenylphosphine from palladium tetrakis(triphenylphosphine). The thus-obtained, activated palladium complex is recovered, after termination of the telomerization and/or oligomerization, by adding 2–6 molar equivalents of triphenylphosphine to the reaction product, distilling the telomer or oligomer therefrom and recovering the thus-regenerated palladium tetrakis(triphenylphosphine) from the distillation residue.

8 Claims, No Drawings

PROCESS FOR THE TELOMERIZATION OR OLIGOMERIZATION OF ACYCLIC CONJUGATED DIOLEFINS

BACKGROUND OF THE INVENTION

This invention relates to a process for telomerization and/or oligomerization of acyclic conjugated diolefins of 4–6 carbon atoms using catalytically active complexes of palladium and triaryl phosphines.

It is conventional to utilize palladium complexes for linear telomerization and/or oligomerization of conjugated diolefins. The catalytically active palladium complexes contain, as ligands, tertiary phosphines, phosphites, or arsines, which may be mixed with other organic compounds, e.g., maleic anhydride or p-benzoquinone. Suitable known cocatalysts are, inter alia, organic bases, for example, quaternary ammonium hydroxides, as disclosed in U.S. Pat. No. 3,769,352, incorporated herein by reference.

Oligomerization, of which the simplest case is dimerization, refers to reaction of a diolefin with another molecule of diolefin. Telomerization refers to the reaction of diolefins with H-acidic compounds, such as alcohols, water, phenols, carboxylic acids, or amines.

Conditions required for oligomerization and/or telomerization depend on the catalyst system and the reactants. (Takahashi et al, Bulletin of the Chemical Society of Japan, Vol. 41, 454–460 (1968).)

To attain high selectivity in the telomerization reaction low reaction, temperatures are advantageous. In the telomerization process, high selectivity is generally achieved by maintaining the concentration of the diolefin at a low level with respect to the H-acidic compound. This can be done, for example, by feeding the diolefin continuously into the reaction mixture as it is consumed. Favorable conditions can be realized only if the catalysts and reactants employed lead to adequately high reaction rates. Otherwise, economically useful conversion rates are obtained only under conditions less favorable for selectivity, i.e., the reactants are contacted with catalyst for a rather long period of time at high temperatures and under high pressures.

The reaction products are separated from the catalyst by distillation at the end of the oligomerization and/or telomerization reaction.

Conditions used during the workup step depend primarily on the activity and stability of the catalysts employed. A distinction can be made, with corresponding advantages and disadvantages, between conditions used with highly active, low-stability catalysts, as disclosed, for example, in DOS (German Unexamined Laid-Open Application) No. 1,955,933 and the corresponding U.S. Pat. No. 3,670,032, and those used with low-activity catalysts, as disclosed by Takahashi et al., "Tetrahedron Letters" 26 (1967):2451.

Although a variety of more or less expensive methods having various disadvantages are known, a genuine need has existed for a process which:

(a) takes place with high space-time yields and selectivities;

(b) permits multiple reuse of palladium catalyst; and (c) produces, for otherwise identical reactions, identical product compositions from recycled catalysts.

It is an object of the invention to provide a process combining the advantages of known catalyst systems without the disadvantages connected therewith.

SUMMARY OF THE INVENTION

This invention relates, in a process for the oligomerization of an acyclic conjugated olefin of 4–6 carbon atoms or for the telomerization thereof with an H-acidic compound, each in the presence of a palladium (triarylphosphine) catalyst, to the improvement which comprises:

(a) employing as catalyst the reaction product of palladium tetrakis(triphenylphosphine) and an amount of an oxidizing agent which removes 1–3.5 molar equivalents of triphenylphosphine therefrom; and (b) regenerating palladium tetrakis(triphenylphosphine) from the reaction product by (i) adding 2–6 molar equivalents of triphenylphosphine, calculated on molar equivalents of palladium, to the reaction product at the termination of the telomerization or oligomerization;

(ii) simultaneously distilling the oligomer or telomer from the reaction product and regenerating palladium tetrakis(triphenylphosphine);

(iii) recovering the palladium tetrakis(triphenylphosphine) from the distillation residue; and (c) repeating step (a) employing a reaction catalyst produced from the recovered palladium tetrakis(triphenylphosphine).

This invention further relates to a process for the oligomerization of an acylic conjugated diolefin or for the telomerization thereof with an H-acidic compound, which comprises employing as the catalyst a palladium(triphenylphosphine) of the formula $Pd(PPh_3)_n$ wherein n is 0.5–3. Such catalysts are produced by the oxidative removal of 0.5 to 3.5 molar equivalents of triphenylphosphine from palladium tetrakis(triphenylphosphine) by treatment of the latter with an oxidizing agent, e.g., $O_2$.

DETAILED DESCRIPTION

Suitable acyclic conjugated diolefins of 4–6 carbon atoms are butadiene, isoprene, piperylene, and 2,3-dimethylbutadiene.

H-acidic compounds are primary and secondary alcohols of 1 to 8 carbon atoms, phenols of 6 to 12 carbon atoms, carboxylic acids of 1 to 12 carbon atoms, and water. The H-acidic compounds are utilized in the telomerization reaction in amounts of 0.5–10 moles, preferably 0.75–2 moles, per mole of conjugated diolefin.

The catalysts are produced by reacting Pd(II) compounds with excess triphenylphosphine, preferably in the presence of a reducing agent. See, for example, L. Malatesta, A. Angoletta, J. Chem. Soc. 1957:1186; and and DOS 1,905,762.

An example of the reaction sequence is:

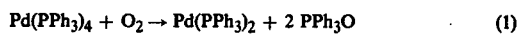

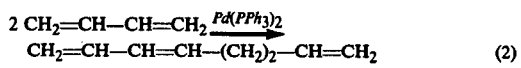

The oligomerization and/or telomerization is conducted as follows:

(1) Preparation of the Active Catalyst

Palladium tetrakis(triphenylphosphine) is suspended in a solvent which is resistant to the oxidizing agent employed and which can optionally be used in a subsequent telomerization reaction, and is treated with an oxidizing agent. During this step, the palladium complex is dissolved. The solution can readily be utilized for oligomerizations or telomerizations. If the oxidizing agent is oxygen, the latter is displaced prior to the subsequent telomerization by an inert gas or, if the diolefin is a gas, by the latter.

If the H-acidic compound cannot be used for the oxidation reaction, owing to instability toward the oxidizing agent, the solvent utilized for the oxidation reaction, for example, methanol, is removed under vacuum at sump temperatures below 40° C. and the complex remaining in the distillation residue is dissolved in the H-acidic compound.

(2) Oligomerization and/or Telomerization Reaction

Oligomerization and telomerization reactions are known, e.g., Takahashi, Shibano, and Hagihira, Bull. Chem. Soc. Japan 41: 454–460 (1968); and DOS 1,807,491.

(2.1) At Atmospheric Pressure or Under Slight Excess Pressure

The solution of complex is agitated in an H-acidic compound (for telomerizations) or in an inert compound (for oligomerizations) in the diolefin atmosphere at atmospheric pressure or under slight excess pressure at temperatures of 0°–100° C. The diolefin is replenished as it is consumed, as indicated by pressure drop. In this type of operation, the end of the reaction is indicated by the cessation of diolefin comsumption.

(2.2) Under Excess Pressure

The diolefin is introduced into an agitator-equipped pressure vessel which contains the complex in an H-acidic compound (for telomerizations) or in an inert compound (for oligomerizations), either in solution or in the solid phase (for oligomerizations). This can be effected by allowing the gaseous diolefin, e.g., butadiene, to be distilled into the pressure vessel, which is cooled with a refrigerating mixture. It is also possible to add the diolefin in metered amounts in the liquid phase, either in incremental portions or continuously, depending on the rate of consumption. The reaction is conducted at temperatures of 40°–140° C. The end of the reaction is apparent from cessation of the pressure drop.

(3) Work Up to Oligomerization or Telomerization Batches

To terminate the telomerization and/or oligomerization reaction, the solution containing oligomerized and/or telomerized products, residual diolefins, solvents or H-acidic compounds, and catalyst, is combined with 2–6 moles of triphenylphosphine per gram atom of palladium, and the mixture is separated by distillation. The sump temperature preferably should not exceed 90° C. to avoid damage to the catalyst.

The palladium tetrakis(triphenylphosphine) thus regenerated is crystallized by heating and digestion in a polar solvent, e.g., methanol. The purified complex is isolated, after cooling the mixture, by filtration, centrifugation or decantation and drying. Each of these steps is to be effected with exclusion of air.

If the oligomerization or telomerization reactions are not conducted successively, this step is best suited for storage. The thus-produced material is stored under dry conditions with exclusion of oxygen, in a dark and cool place.

Palladium tetrakis(triphenylphosphine) is used in amounts of 1–100 moles, preferably 5–20 moles, per 100,000 moles of diolefin.

It will be appreciated that triphenylphosphine is readily available and that the use of palladium tetrakis(triphenylphosphine) is convenient. However, other corresponding palladium complexes can be used, contemplated equivalents including $Pd(Ar_3P)_4$, wherein Ar is tolyl, chloro-phenyl, methoxy-phenyl, naphthyl.

Suitable oxidizing agents are compounds capable of oxidizing triphenylphosphine to triphenylphosphine oxide, for example, hydrogen peroxide, alkyl and alkanoyl hydroperoxides of up to 10 carbon atoms and dialkyl and dialkanoyl peroxides of up to 10 carbon atoms e.g., cyclohexan-hydroperoxide, cumene-hydroperoxide, diethyl-peroxide, di-tert.-butyl-peroxide, peracetic acid, perbenzoic acid. See "Methoden der organischen Chemie" (Methods of Organic Chemistry), Houben-Weyl; "Organische Phosphorverbindungen" (Organic Phosphorus Compounds) part 1, page 141, Georg Thieme Verlag publishers, Stuttgart). The preferred oxidizing agent is molecular oxygen.

Suitable media for the oxidation are polar organic liquids, especially lower alcohols, most preferably methanol. Other polar organic liquids include but are not limited to acetone, tetrahydrofurane.

The palladium tetrakis(triphenylphosphine) is suspended in the selected liquid. For each gram of complex, 10–100 ml., preferably 30–50 ml., of liquid is utilized.

The oxidation reaction takes place at 0°–100° C., preferably at 20°–40° C. If the same liquid is used for the oxidation reaction and the dimerization reaction, the same volume can also be utilized for both reactions. In this case, both reactions are also preferably conducted at the same temperature.

The amount of the oxidizing agent is chosen so that 1–3.5, preferably 1.5–3.0 molar equivalents of triarylphosphine are removed from the palladium tetrakis(triphenylphosphine) by oxidation to triarylphosphine oxide. The yellow complex dissolves during the oxidation. The triarylphosphine oxide produced by the oxidation does not interfere with the telomerization or oligomerization reaction.

In a preferred embodiment of the process of this invention, air is introduced into the suspension, but the suspended complex must be well agitated. The oxidation reaction is terminated by interrupting the air feed and displacing the oxygen by an inert gas, for example, nitrogen, as soon as the complex has dissolved. Continuation of the oxidation impairs the catalyst activity and is to be avoided.

The catalyst concentrate present after the oxidation is optionally diluted with the solvent used for the dimerization reaction. If the oxidation reaction is conducted in a liquid which interferes with the dimerization, this liquid is removed under vacuum at temperatures not exceeding 60° C., preferably not exceeding 40° C. The residue contains the complex in its active, readily-soluble form. The concentrate and the residue are to be kept under an oxygen-free atmosphere.

The oligomerization and/or telomerization is terminated when inadequate amounts of diolefins are being converted.

The process of this invention permits simple recovery and/or activation of an expensive palladium complex catalyst by treatment with oxidizing agents according to the invention. The resulting favorable effect on catalytic activity has not been known heretofore, nor been suggested by the state of the art. In accordance with pertinent prior art, oxygen is thought to be deleterious to palladium-containing catalysts for butadiene oligomerization and/or telomerization (U.S. Pat. No. 3,670,032).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1 (COMPARATIVE EXAMPLE)

Ethanol (100 ml., 79.4 g.) is charged, together with 575 mg. (0.5 millimole) of palladium tetrakis(triphenylphosphine), into a reactor. The reaction chamber is purged with nitrogen. Thereafter, butadiene is passed through under atmospheric pressure at 25°–30° C. During a reaction time of 12 hours, 7 g. of butadiene is absorbed by the reaction mixture. The complex, at this point, is present in the reaction medium in essentially undissolved form. The reaction mixture, as determined by gas chromatography, contains minor amounts of 1,3,7-octatriene, 3-ethoxy-1,7-octadiene, and 1-ethoxy-2,7-octadiene.

Yield:
8 g. — 1-Ethoxy-2,7-octadiene
0.6 g. — 3-Ethoxy-1,7-octadiene
0.1 g. — 1,3,7-Octatriene

EXAMPLE 2

At room temperature, 100 ml. (79.4 g.) of ethanol and 575 mg. (0.5 millimole) of palladium tetrakis(triphenylphosphine) are charged into a reactor. Air is passed through for about one hour. The catalyst almost completely dissolved during this step. Thereafter, air is displaced by nitrogen and butadiene is simultaneously introduced. Vigorous consumption of butadiene commences immediately. After a reaction period of 12 hours, approximately 102 g. of butadiene has been absorbed. By gas chromatography analysis, the reaction mixture contains the desired reaction product but in more than 10 times the yield of Example 1.

Yield:
83.5 g. — 1-Ethoxy-2,7-octadiene
4.0 g. — 3-Ethoxy-1,7-octadiene
5.3 g. — 1,3,7-Octatriene The reaction mixture is combined with 262 mg. (1 millimole) of triphenylphosphine and distilled under high vacuum at a maximum sump temperature of 85° C. The product isolated is 1-ethoxy-2,7-octadiene (64 g., 96-97% purity). The residue from the distillation (18 g.) is treated with a solution of 1.05 g. of triphenylphosphine in 15 ml. of boiling methanol. By cooling to room temperature, a yellow crystalline precipitate is obtained which is vacuum-filtered and washed with a small amount of methanol. The crystals are separated under a nitrogen atmosphere.

Yield: 650 ml. of yellow crystals which are used as the complex in Example 3.

EXAMPLE 3

Ethanol (100 ml., 79.4 g.) is utilized, together with 650 mg. of the palladium complex precipitated and isolated from the distillation residue of Example 2, and activated and reacted with butadiene as described in Example 2.

Yield:
74.0 g. — 1-Ethoxy-2,7-octadiene
2.8 g. — 3-Ethoxy-1,7-octadiene
7.0 g. — 1,3,7-Octatriene The reaction mixture is combined with 262 mg. of triphenylphosphine and fractionally distilled. The product is 66 g. of 1-ethoxy-2,7-octadiene (degree of purity ≈98%). The distillation residue weighs 6.5 g.

EXAMPLES 4–7

In each case, 0.5 millimole of palladium tetrakis(triphenylphosphine) is suspended in 100 ml. of isopropanol. In Examples 5 and 7, the suspension is agitated at 30° C. under atmospheric pressure in an oxygen atmosphere until the complex has been dissolved. Thereupon, the oxygen is displaced by nitrogen.

In Examples 4 and 5, 56 g. of butadiene is introduced, and simultaneously condensed, into an autoclave cooled to −10° C. In Examples 6 and 7, the solution of complex is agitated in a pure butadiene atmosphere at an excess pressure of 190 mm. of water.

After a reaction time of 8 hours, 2 millimoles of triphenylphosphine is added to the reaction mixture of Example 7. The reaction mixtures are distilled with exclusion of oxygen at 0.2 torr (mm. Hg), and the reaction products are analyzed by gas chromatography.

The results are given in Table I. No substances other than the starting raw materials and the compounds indicated in the table were detected.

It can be seen from comparison of Example 4 with Example 5 and of Example 6 with Example 7 that the oxygen-activated catalyst exhibits higher activity. Example 7 demonstrates that even telomers which are obtainable only with difficulty, e.g., of a secondary alcohol, can be produced using these reusable catalysts.

TABLE I

| Example No. | Catalyst | Reaction Vessel | Reaction Temperature °C. | Reaction Time h. | Yield in Grams | | |
|---|---|---|---|---|---|---|---|
| | | | | | 1-Isopropoxy-2,7-octadiene | 3-Isopropoxy-1,7-octadiene | Dimers* |
| 4 (Comp. Ex.) | Pd(PPh$_3$)$_4$ | Autoclave | 110 | 8 | 0.2 | 0.0 | 7.4 |
| 5 | Pd(PPh$_3$)$_2$ | Autoclave | 100 | 4 | 0.6 | 0.0 | 49.0 |
| 6 (Comp. Ex.) | Pd(PPh$_3$)$_4$ | Glass Flask | 30 | 8 | 0.1 | 0.0 | 0.0 |
| 7 | Pd(PPh$_3$)$_2$ | Glass Flask | 30 | 8 | 5.6 | 0.1 | 1.6 |

*1,3,7-Octatriene and small amounts of 4-vinylcyclohexene.

EXAMPLE 8

Under an $N_2$ atmosphere, 5 ml. of isopropanol is added to the distillation residue of Example 7. The mixture is briefly heated to reflux and then allowed to cool to room temperature and later in ice water to 0° C. The mixture is decanted from the resulting crystalline slurry. The residue is crushed with a rubber scraper and stirred together with 100 ml. of isopropanol to obtain a fine suspension which is agitated at 30° C. in an oxygen atmosphere until a clear solution is produced. Otherwise, the procedure of Example 7 is followed. There is obtained 5.7% of 1-isopropoxy-2,7-octadiene and 1.5% of 1,3,7-octatriene.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the oligomerization of an acyclic conjugated diolefin of 4–6 carbon atoms and for the telomerization thereof with a $C_{1-8}$ alkanol, each in the presence of a palladium (triarylphosphine) catalyst, the improvement which comprises:
    (a) prior to the oligomerization and telomerization, reacting palladium tetrakis(triphenylphosphine) with an amount of molecular oxygen which removes 1.3–5 molar equivalents of triphenylphosphine therefrom;
    (b) reacting the alkanol and the diolefin using as a catalyst the reaction product of step a);
    (c) regenerating, with the exclusion of air, palladium tetrakis(triphenylphosphine) from the reaction product of (b) by
    (i) adding 2–6 molar equivalents of triphenylphosphine, calculated on molar equivalents of palladium, to the reaction product at the termination of the telomierzation and oligomerization, b);
    (ii) simultaneously distilling oligomer or telomer from the reaction product and regenerating palladium tetrakis(triphenylphosphine);
    (iii) recovering the palladium tetrakis(triphenylphosphine) from the distillation residue; and
    (d) repeating step a) employing a reaction catalyst produced from the recovered palladium tetrakis(triphenylphosphine).

2. The process of claim 1 wherein, in step (a), the oxidizing agent converts triphenylphosphine to triphenylphosphine oxide.

3. The process of claim 1, wherein 1–3.5 moles of triphenylphosphine is oxidized per mole of palladium tetrakis(triphenylphosphine).

4. The process of claim 1, wherein 1.5–3.0 moles of triphenylphsophine is oxidized per mole of the palladium tetrakis(triphenylphosphine) recovered in step (c).

5. The process of claim 1, wherein the conjugated diolefin is butadiene.

6. The process of claim 1, wherein 3–6 molar equivalents of triphenylphosphine per molar equivalent of palladium are used in step (c).

7. The process of claim 1, wherein 5–20 moles of palladium tetrakis(triphenylphosphine) is used per 100,000 moles of diolefin.

8. In a process for the oligomerization of an acyclic conjugated diolefin of 4–6 carbon atoms in the presence of a palladium (triarylphosphine) catalyst, the improvement which comprises:
    (a) prior to the oligomerization, reacting palladium tetrakis (triphenylphosphine) with an amount of molecular oxygen which removes 1–3.5 molar equivalents of triphenylphosphine therefrom;
    (b) oligomerizing the diolefin using as a catalyst the reaction product of step (a);
    (c) regenerating, with the exclusion of air, palladium tetrakis(triphenylphosphine) from the reaction product of (b) by
    (i) adding 2–6 molar equivalents of triphenylphosphine, calculated on molar equivalents of palladium, to the reaction product at the termination of the oligomerization, (b);
    (ii) simultaneously distilling oligomer from the reaction product and regenerating palladium tetrakis(triphenylphosphine);
    (iii) recovering the palladium tetrakis(triphenylphosphine) from the distillation residue; and
    (d) repeating step (a) employing a reaction catalyst produced from the recovered palladium tetrakis(triphenylphosphine).

* * * * *